United States Patent [19]
Sicurelli, Jr. et al.

[11] Patent Number: 5,741,139
[45] Date of Patent: *Apr. 21, 1998

[54] FLEXIBLE POST IN A DENTAL POST AND CORE SYSTEM

[75] Inventors: Robert J. Sicurelli, Jr., Muttontown; Samuel Masyr, Brooklyn, both of N.Y.

[73] Assignee: Tru-Flex Post Systems, Inc., Muttontown, N.Y.

[*] Notice: The term of this patent shall not extend beyond the expiration date of Pat. No. 5,518,399.

[21] Appl. No.: 651,805

[22] Filed: May 20, 1996

Related U.S. Application Data

[63] Continuation-in-part of Ser. No. 126,631, Sep. 27, 1993, Pat. No. 5,518,399.

[51] Int. Cl.⁶ ..................................................... A61C 5/08
[52] U.S. Cl. ..................................................... 433/220
[58] Field of Search ............................. 433/175, 220, 433/221, 225

[56] References Cited

U.S. PATENT DOCUMENTS

| | | | |
|---|---|---|---|
| 622,670 | 4/1899 | Dwight | 433/221 |
| 732,922 | 7/1903 | Clark | 433/221 |
| 822,582 | 6/1906 | Carmichael | 433/220 |
| 1,218,289 | 3/1917 | Maker | 433/220 |
| 3,949,476 | 4/1976 | Kahn | 32/12 |
| 4,172,867 | 10/1979 | Devault | 264/16 |
| 4,622,012 | 11/1986 | Smoler | 433/211 |
| 4,631,030 | 12/1986 | von Weissenfluh | 433/149 |
| 4,645,457 | 2/1987 | Goldman | 433/220 |

(List continued on next page.)

FOREIGN PATENT DOCUMENTS

| | | |
|---|---|---|
| 0076086 | 9/1982 | European Pat. Off. |
| 1457914 | 11/1966 | France. |
| 2587197 | 9/1985 | France. |
| 8515527 | 10/1985 | France. |
| 2645431 | 7/1988 | France. |
| 2626167 | 1/1989 | France. |
| 1541209 | 7/1969 | Germany. |
| 3411366 | 10/1985 | Germany. |
| 3643219 | 6/1988 | Germany. |
| 3643219 A1 | 6/1988 | Germany. |
| 3825601 | 3/1989 | Germany. |
| 1457914 | 11/1966 | Switzerland. |
| 669514 | 3/1989 | Switzerland. |
| 1277950 | 12/1986 | U.S.S.R.. |
| 1519684 | 11/1989 | U.S.S.R.. |
| 1302022 | 1/1973 | United Kingdom. |
| 2214087 | 8/1989 | United Kingdom. |
| WO 91/07142 | 5/1991 | WIPO. |

OTHER PUBLICATIONS

Brochure, "C–Post", Bisco Company, Itasca, Illinois, undated.

Advertisement "Flexi–Post & Flexi–Flange", Essential Dental Systems, 89 Launing Street, S. Hackensack, NJ 07606 undated.

"A Comparison of Intracanal Stresses in a Post–Restored Tooth Utilizing the Finite Element Method", Cailleteau, J., et al., Journal of Endodontics, vol. 18, No. 11, pp. 540–544, Nov. 1992.

Primary Examiner—Cary E. O'Connor
Attorney, Agent, or Firm—Alfred M. Walker

[57] ABSTRACT

A dental post and core system having an inelastic flexible post. The post, which may be radiopaque and tooth colored, conforms to the natural curved contours of a root canal to reduce machining of the tooth and mechanical weakening of the tooth structure. The post is made of a material having a plurality of fibers, wherein at least one or more of the fibers is non-axially aligned with respect to a straight axis extending from a coronal end to an apical end of a root of the tooth, such as non-axially aligned fibers twisted together, or such as randomly dispersed fibers in a plastic composite. Since not all the fibers are axially aligned, increased strength is achieved by reduction of the possibility of an axially extending fault crack in the resin of the post.

38 Claims, 3 Drawing Sheets

U.S. PATENT DOCUMENTS

| | | | |
|---|---|---|---|
| 4,684,555 | 8/1987 | Neumeyer | 428/36 |
| 4,696,646 | 9/1987 | Maitland | 433/149 |
| 4,726,770 | 2/1988 | Kurer | 433/229 |
| 4,738,616 | 4/1988 | Reynaud | 433/220 |
| 4,759,714 | 7/1988 | Szeguary | 433/221 |
| 4,778,388 | 10/1988 | Yuda | 433/221 |
| 4,778,389 | 10/1988 | Salvo | 433/221 |
| 4,934,936 | 6/1990 | Miller | 433/220 |
| 4,936,776 | 6/1990 | Kwiakowski | 433/220 |
| 4,952,150 | 8/1990 | Schiwiora | 433/220 |
| 4,990,090 | 2/1991 | Roane | 433/220 |
| 5,007,837 | 4/1991 | Werly | 433/226 |
| 5,030,093 | 7/1991 | Mitnick | 433/164 |
| 5,073,112 | 12/1991 | Weil | 433/221 |
| 5,074,792 | 12/1991 | Bernadat | 433/220 |
| 5,088,927 | 2/1992 | Lee | 433/224 |
| 5,092,773 | 3/1992 | Levy | 433/224 |
| 5,116,227 | 5/1992 | Levy | 433/216 |
| 5,145,373 | 9/1992 | Roane | 433/221 |
| 5,165,893 | 11/1992 | Thompson | 433/224 |
| 5,284,443 | 2/1994 | Weil | 433/224 |
| 5,320,530 | 6/1994 | Fong | 433/119 |
| 5,326,263 | 7/1994 | Weissman | 433/224 |
| 5,328,372 | 7/1994 | Reynaud et al. | 433/220 |
| 5,407,973 | 4/1995 | Hasegawa | 523/116 |
| 5,518,399 | 5/1996 | Sicurelli | 433/220 |

FLEXIBLE POST IN A DENTAL POST AND CORE SYSTEM

This application is a continuation-in-part of application Ser. No. 08/126,631 filed Sep. 27, 1993 and now U.S. Pat. No. 5,518,399 to be issued May 21, 1996.

BACKGROUND OF THE INVENTION

The present invention generally relates to a dental post and core system for endodontically-treated teeth. More specifically, this invention relates to a passive dental post and core system having a flexible inelastic post, wherein the post is made from a material having a plurality of distributed fibers, wherein at least one of the fibers extends non-axially aligned with respect to a straight axis extending from the apical end to the opposite coronal end of a root of a tooth. For example, the fibers may be a bundle of fibers, a longitudinally twisted bundle, a twisted braid, a woven lattice, a helically wrapped bundle of fibers, or a composite of randomly dispersed fibers in a binder.

In each case, at least one of the fibers extends non-axially aligned with respect to the straight axis of a root of a tooth.

For example, in a bundle of fibers, while some of the fibers may extend parallel to the straight axis of the root, at least one or more of the fibers extend in an axial direction which is not parallel to straight axis of a root of a tooth. That is, at least one or more of the fibers extends in a transverse or angled direction away from the straight axis of the root of a tooth.

With respect to a longitudinally twisted bundle, a twisted braid, a helically wrapped bundle of fibers, the twisting or helical wrap of the fibers causes many, but not necessarily all, of the fibers to extend non-axially. Concerning a woven lattice of fibers, while one set of fibers could extend axially parallel to the straight axis of the root, the other intersecting set of fibers extends in a direction which is non-axially aligned with respect to the straight axis of the root. Even if most of the weft of a weave of a plurality of fibers extends parallel to the straight axis of the root, at least one or more fibers constituting the warp of the weave of fibers extends non-axially with respect to the straight axis of the root of the tooth.

Moreover, concerning a composite of randomly dispersed fibers, there is always the possibility of one or more of the fibers being axially aligned to the straight axis of the root of a tooth. However, in order to be randomly dispersed, at least one or more of the fibers extends non-axially with respect to the straight axis of the root of a tooth.

Preferably, the post is radiopaque and bears a color simulating that of a natural tooth.

Rigid dental post and core systems are widely utilized to restore endodontically-treated teeth. Post and core restorations are routinely used to create an adequate foundation for the final restorative step, which may be a crown, onlay, or a fixed partial denture abutment. Generally, a post is provided for retention and lateral stability of the restoration. The core provides support for the crown. Two general types of post and core systems are known in the art: "active" or screw-in type systems and "passive" type systems. Active post and core systems mechanically engage the walls of the root canal and tooth dentin. Passive post and core systems are bonded in a reformed root canal utilizing cements and the like.

Two major problems are encountered when restoring an endodontically-treated tooth. Firstly, the tooth is more susceptible to fracture, and secondly, there is generally less coronal structure with which to work. The greater susceptibility of a tooth to fracture after endodontia may result from the tooth being more brittle. However, studies of the changing mechanical properties of pulpless teeth do not generally support this theory equating dryness with reduced mechanical strength. It appears that the greater susceptibility for fracture in an endodontically treated tooth results from mechanical weakening of the tooth during root canal therapy and refinement of the root canal. Improvements in restoration techniques that reduce mechanical weakening are therefore desirous.

An endodontically-treated tooth is generally severely compromised either due to trauma or neglect. Thus, traumatic fractures, removal of old restorations and carious tissue, and preparation of root canal access may not leave enough tooth to maintain the "dome effect" of the tooth or to retain a crown.

The stress concentrations in a tooth resulting from the rigid post and core systems of the prior art also play a vital role in tooth fracture. Stress concentrations can be impacted through system design and/or restoration techniques. Various studies and investigations into the susceptibility of endodontically-treated teeth to fracture and the contribution of rigid dental post and core systems to such fracture have been conducted. *A Comparison of Intracanal Stresses in a Post Restored Tooth Utilizing the Finite Element Method*, Cailleteau, Johnny G., Rieger, Monty R. and Akin, J. Ed, Journal of Endodontics, Vol. 18, No. 11, November 1992, pp. 540–544, reports that placement of a rigid post within a tooth alters the pattern of stress along the root canal as compared with an intact tooth. Instead of strengthening the tooth the post stiffens the coronal posted section and shifts the flexure point apically. The effect of this stiffening causes the nonposted apical portion of the tooth to deform at the lost apex, resulting in a stress increase in that portion of the canal wall. Also, the cyclic loading and unloading of an incisor during mastication requires consideration of fatigue failure. Since the maximum bending stresses occur in connection with the apex of the post, any inclusions or defects within the wall of the dentin near the apical end of the post would create stress concentrations that increase the risk of a fatigue crack formation. Defects and microfractures introduced during endodontic treatment and post access preparation could become areas contributing to stress concentrations. Studies have also shown that more intact tooth structure provides better resistance to fracture than a metallic post. There is also evidence that stresses in the tooth tend to increase as the post diameter increases.

A flexible post eliminates these problems. A post and core system utilizing a flexible post shifts the stress concentrations coronally, eliminates the introduction of defects during post access preparation and lost placement, and leaves more of the tooth intact.

The main function of a post is to provide retention to the core. Relieved of its expectation to facilitate resistance to tooth fracture, the post can be designed to optimize its retentive properties. Several factors govern the retentiveness of endodontic posts. The shape of the post and its length are among the essential factors. Tapered dowels have been found to be significantly less retentive than parallel-sided posts. A serrated 5.5-mm parallel-sided dowel was found more retentive than an 8-mm tapered post. Tapered posts provide high shoulder stresses but have an undesirable wedging effect. The wedging effect results in part from the prior art placement of a straight rigid post in a naturally curved and varying diameter root canal. Active posts are very retentive, but may impose too much stress on the tooth, especially compromised teeth. Thus it appears that a passive, serrated, parallel-sided post is a preferred structure for dental post and core systems. A flexible, passive, serrated parallel-side post provides the previously-mentioned advantages in preventing tooth fracture and additionally permits the post to extend for a greater length into the root canal for improved retention.

In addition to post shape and length, adequate retention is a function of cementing mechanisms. Various cementing medium have been studied. Utilization of low viscosity resin cement in combination with smear layer removal can be considered a universal post cementation technique. In addition to good retention, this cementing technique offers the benefits of a cement with very little resistance to post insertion, thereby minimizing stresses applied to tooth structure during cementation. HoWever, the invention of the present disclosure is not limited by the cementing process used.

An elastic, wire pin having a plurality of flexible, radially extending fins along its length is disclosed in German Patent No. DE 3643-219 to Weisskircher. While providing some advantages over the prior art rigid post, the "high degree of elasticity" of the Weisskircher pin will cause it to try and retain its initial shape in the root canal. During and after placement, flexing of the pin will cause the apical end of the pin to lay against the wall of the root canal. Stress concentrations in the tooth as known for rigid posts will thereby be induced. A pin formed from wire also has low retention characteristics and tends to rotate within the root canal. Radial fins are utilized in the Weisskircher disclosure to resist rotation of the wire pin. However, these radial fins may become further sources of stress concentrations and fatigue failure as the wire pin rotates. No prior art known to the present Applicants discloses or suggests a flexible post in a dental post and core system that is flexible and inelastic, that conforms to the shape of the root canal to eliminate the stress concentrations that facilitate tooth fracture.

U.S. Pat. No. 4,778,389 to Salvo discloses a dental post construction to eliminate lateral stress in a tooth wherein a rigid, split post is formed by parallel sections joined at a marginal top portion of the post head.

U.S. Pat. No. 5,073,112 to Weil discloses a dental post having an active portion and a passive portion.

U.S. Pat. No. 5,074,792 to Bernadat discloses a passive post and core system comprising a rigid peg disposed in a porous sheath formed of high-strength filaments, wherein the peg has a set of parallel radially extending fins extending from the peg. The filaments in Bernadat are found in the sheath surrounding the peg, not in the peg itself.

U.S. Pat. No. 732,922 of Clark describes a pin for teeth which is flexible, but only by virtue of the fact that the pin includes a base and two tapered pins extending from the base, with a space therebetween, so that the tapered pins can close toward each other within the space.

U.S. Pat. No. 4,952,150 of Schiwiora discloses a tooth root post which includes a tip of solid flexible metal or metal alloys. In contrast, in the present invention, the root post is made of a plurality of metallic or non-metallic fibers, as opposed to a solid piece of metal.

U.S. Pat. No. 4,934,936 of Miller describes a serrated dental post. U.S. Pat. Nos. 622,670 of Dwight and 1,218,289 of Maker both disclose solid threaded posts with a core spacer neck extending therearound.

International Search Publication No. WO 91/07142 (PCT/FR90/00831) to Reynaud et al. discloses a dental post and core system having a post formed from equally-tensioned fibers of composite material. In Reynaud, the fibers of the composite material are all laid axially within the post and embedded within a resin. Because the fibers are equally tensioned and extend only axially aligned and continuous, any modification of the post in Reynaud may cause a major spreading, continuous, fault line crack in the resin of the post, thus losing integrity of the Reynaud post.

In contrast, in the present invention at least one or more of the fibers extends in a direction which is non-axially aligned with respect to the straight axis extending from the apical end to the opposite coronal end of a root of a tooth. Because there is a plurality of directions with respect to the fibers, such as at least one fiber running non-axially, the possibility of a spreading, continuous fault line crack is significantly reduced, thereby achieving unexpected beneficial results not suggested in Reynaud.

U.S. Pat. No. 4,936,776 to Kwiatkowski discloses a translucent post and core structure to minimize gingival discoloration adjacent a dental restoration.

U.S. Pat. No. 3,949,476 to Kahn discloses a "direct" method of restoring an abraded or broken tooth.

Swiss Patent No. 1,457,914 to Stomatology Research Institute discloses a method of making a pin stump insert.

West German Patent No. 1,541,209 to Kurer discloses the now conventional threaded, screw-in type active post.

Currently-marketed dental post and core systems such as the FLEXI-POST; the DENTATUS POST, the RADIX POST and the BRASSELEAR screw posts all advocate screwing threaded rigid posts into straight paths machined into the tooth dentin. The present day posts are also generally formed from rigid metals such as steel, titanium and other alloys which do not flex in the same manner as a natural tooth. This differential in flexibility between the natural tooth and the post may cause tooth fracture when the restored tooth is stressed during mastication or from trauma. Cast posts are subject to these same limitations and require an additional laboratory fee and an additional visit to the dentist to complete the procedure.

A means to quickly and easily identify the components of a post and core system is also needed in the prior art. Presently, there is either no color-coding of post and core systems or the color identification consists of an inconspicuous dot of color. Brightly-colored means of identifying post and core systems would significantly advance the art. The lack of a color protocol in the prior art creates confusion, eye strain and a sloppy work environment. The inability to readily identify each post and core by sight creates problems before, during and after the procedure is completed. Firstly, before the procedure is initiated the dentist and staff must select the post and core and isolate it from others that may be very close in size. During the procedure the dentist must carefully avoid confusing the selected post and core. After the procedure the used and unused devices must be readily identified for contamination control. Further, a post and core system installed by one dentist may later require an emergency or other procedure by a different dentist in a completely different part of the world. Color-coded identification would eliminate uncertainty and guesswork.

The post and core system of the present invention overcomes all of these limitations of the prior art.

SUMMARY OF THE INVENTION

The present invention is a dental post and core system that includes a flexible post. The flexible post conforms to the curvature of the root canal during placement and reduces mechanical weakening of an endodontically-treated tooth by eliminating stress concentrations at the apical end of the post, by reducing the size of canal access preparations and by allowing more intact tooth to be retained.

The present invention also provides a method of restoring an endodontically-treated tooth that reduces the time and equipment needed during a procedure and lessens the chance that a dentist will perforate or fracture the canal wall during placement of a post.

In a preferred embodiment of the dental post and core system of the present invention the post includes a core spacer and a flexible, post reinforcing rod extending apically from the core spacer. The core spacer may be flexible, resilient or otherwise deformable and may be selectively attachable or integrally formed with a post reinforcing rod. A core may be selectively attached to the upper portion of the core spacer, integrally formed with the core spacer or built-up to custom specifications.

A further embodiment of the present invention is a mutable flexible post. The mutable post of the present invention comprises a bundle of reinforced plastic or metal fibers that have at least one or more fibers which extends non-axially aligned with respect to the straight axis extending from the coronal end to the apical end of a tooth. The post may also be selectively flared at the coronal aspect to provide a core seat or to provide extra surface area to scaffold a core.

OBJECTS OF THE INVENTION

An object of this invention is to provide a passive and bondable dental post and core system for endodontically-treated teeth.

Another object of this invention is to provide a dental post and core system that reduces the susceptibility for tooth fracture in endontically-treated teeth.

A further object of this invention is to provide a method for restoring endodontically-treated teeth that reduces the susceptibility for tooth fracture.

Another object of the present invention is to provide a dental post and core system that reduces the mechanical weakening of tooth structure by relieving stress concentrations.

Another object of the present invention is to provide a dental post and core system that reduces the risk of a dentist creating perforations and microfractures during post placement.

It is also an object of the present invention to provide a flexible post in a dental post and core system that automatically adjusts to the contours of a root canal during placement.

Another object of this invention is to provide a post and core system having a flexibility that closely mimics the flexibility of the pulp and dentin tissue of a natural tooth.

Another object of the present invention is to provide a dental post and core system that reduces the amount of time required to restore an endodontically-treated tooth.

It is also an object of this invention to provide a dental post and core system that can be safely and quickly installed by any dentist in a single visit.

Another object of this invention is to provide a dental post and core system formed from material that can be readily shaven to accommodate canal irregularities and in-between root canal sizes without loosing its physical properties.

Another object of this invention is to provide a dental post and core system that is radiopaque.

Another object of this invention is to provide a method of restoring endodontically-treated teeth that eliminates drilling for post placement and that can be installed using inexpensive, readily available endodontic drills.

Another object of this invention is to provide a post in a dental post and core system that fits intimately within a root canal and that accepts standard dental cements.

Another object is to provide a color-coded dental post and core system for identification purposes.

A further object of the present invention is to provide dental post and core system that substantially fits all teeth.

It is another object of the present invention to provide a dental post and core system that can be provided in standardized sizes for mass production efficiencies.

A still further object of this invention is to provide a restoration system for teeth previously classified as hopeless and difficult, such as hemisected and dilacereted teeth and other conditions of extreme loss of tooth structure.

These and other objects and advantageous of the improved dental post and core system of the present invention will be apparent to those skilled in the art from the following description of preferred embodiments, claims and appended drawings.

DESCRIPTION OF THE PREFERRED EMBODIMENTS

Figure 1:
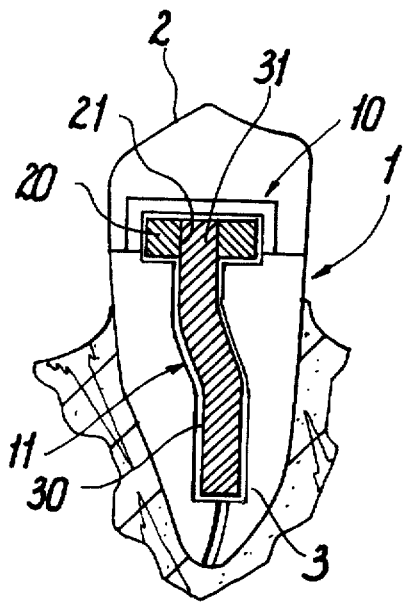
FIG. 1 is a lateral cross-sectional view of the first preferred embodiment of the dental post and core system of the present invention.

FIG. 1 illustrates in a lateral cross-sectional view a first preferred embodiment of the dental post and core system 1 of the present invention. First system 1 generally comprises a core 10 and flexible post 11. Post 11 includes a core spacer 20 and a flexible inelastic post reinforcing rod 30 extending apically from the core spacer 20. The post reinforcing rod 30 may be cylindrical or tapered. Further, core spacer 20 may be flexible and/or resilient. In the first dental post and core system 1, core spacer 20 and reinforcing rod 30 are shown to be separately constructed. A bore 21 in core spacer 20 selectively engages an upper portion 31 of post reinforcing rod 30.

However, core spacer 20 and reinforcing rod 30 may be integrally formed without departing from the spirit and scope of the present invention. The separable construction of core spacer 20 and the reinforcing rod 30 permits fabrication of built-up post and core systems 1 in a variety of configurations from readily identifiable components. Core 10 is seated on the core spacer 20 and a crown 2, for example, is placed over the core 10, as known in the art.

The teachings of the present invention may be utilized for restoration of multi-rooted teeth having two, three or four diverging canals. In the second dental post and core system 1 for a double-rooted tooth illustrated in FIG. 2 it can be seen that second system 1 includes a second core spacer 20 having two bores 21a, 21b, which engage respective flexible post reinforcing rods 30.

The advantages of a flexible post 11 in a dental post and core system are numerous. Firstly, a flexible post 11 can follow the contours of the root canal 3. This method of placement eliminates or reduces the amount of drilling required for root canal therapy and for preparation of the canal access. The reinforcing rods 30 can be appropriately sized to permit use of commonly-used dental drills. More intact tooth is left in place which has been shown to provide the best resistance to a tooth fracture.

The flexible inelastic post reinforcing rod 30 of the present invention also eliminates stress concentrations in a canal wall and dentin due to the apical lateral movement of rigid and elastic posts. Utilizing a flexible post 11, the intracanal stress at the apical level is shifted coronally to the area of maximum stress. The core spacer 20 absorbs the intracanal stresses by deformation of the body of the core spacer 20. Core spacer 20 therefore can be seen to serve as both a seat for the core 10 and as a stress absorber.

A flexible post 11 also reaches further apically which provides greater retention. This is specifically applicable to the restoration of teeth that have suffered extreme loss of tooth structure where to gain adequate retention the length of the post must enter the curved portion of the root canal 3.

Figure 3:
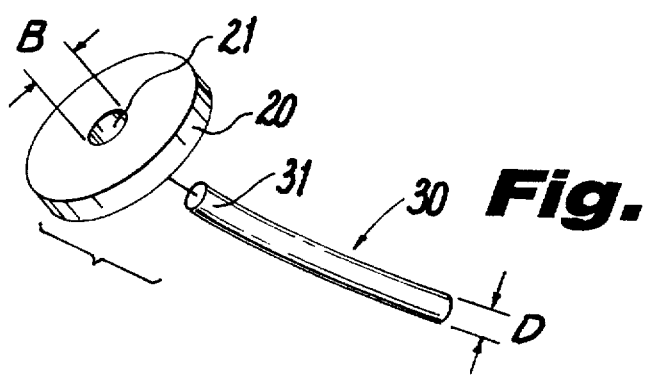
FIG. 3 is a perspective, exploded view of a first core spacer and a first post reinforcing rod of the present invention.

In the first preferred embodiment of the flexible post 11 in the first dental post and core system 1 of the present invention, illustrated in an exploded, perspective view in FIG. 3, the core spacer 20 and the flexible post reinforcing rod 30 are formed from identical material. This, however, should not be understood to be a limitation of the present invention.

The core spacer 20 may be formed of a first material to optimize its stress resistance characteristics; reinforcing rod 30 may be formed of a second material to optimize its retention characteristics.

Core spacer 20 and post reinforcing rod 30 are preferably formed from reinforced plastics, such as fiberglass polyester composites similar to those used win the construction of fishing poles, flexible ceramic resin composites, graphites, teflons, polycarbonates and the like. Metals, such as metal oxides, metal salts or pure or alloyed metals like gold, silver titanium, steel, platinum, palladium and the like, can be processed into fibers and bound in a matrix of resin or other binders for fabrication of the core spacer 20 and post reinforcing rod 30. The flexibility of these materials is close to the flexibility of the natural tooth and therefore will reduce the flexibility differential of the intact tooth and the inserted post 11.

Fiberglass polyester composites and the like, such as ceramic resins, graphite, graphite composites, teflons, polycarbonates, silicon carbide, polyamide, zirconium and aluminum silicate are also well suited for in-office etching of the surfaces of the core spacer 20 and reinforcing rod 30 for better and stronger cementation. Reinforcing rod 30 may also be treated with dental adhesives and bonding agents such as silane urethane, bisgma and acrylic resins to increase retention. Core spacer 20 and post reinforcing rod 30 also preferably include an appropriate amount of radiopaque material such as titanium oxide, barium sulfate and other materials known in the dental industry to insure X-ray documentation and render the object opaque to radiographic imaging.

The first preferred embodiment of the flexible post 11 is preferably color coded for identification purposes. In the first preferred flexible post 11, the core spacer 20 and reinforcing rod 30 are color identified according to the inside diameter of the bore 21 in core spacer 20, identified in FIG. 3 by the letter "B", and the outside diameter of the reinforcing rod 30, identified in FIG. 3 by the letter "D". In the preferred embodiment the reinforcing rods 30 are formed having the following diameters "D": 0.036 inch, 0.040 inch, 0.050 inch, 0.060 inch, and 0.070 inch. The bores 21 of the respective core spacers 20 have a corresponding bore diameter "B" (marginally larger than rod diameter "D") for snug engagement of the spacer 20 to an upper portion 31 of the post reinforcing rod 30. Bright colors are preferably used.

The following color protocol is preferred:

| "D" | Color |
| --- | --- |
| inch | White |
| inch | Yellow |
| inch | Red |
| inch | Blue |
| inch | Green |

Figure 2:
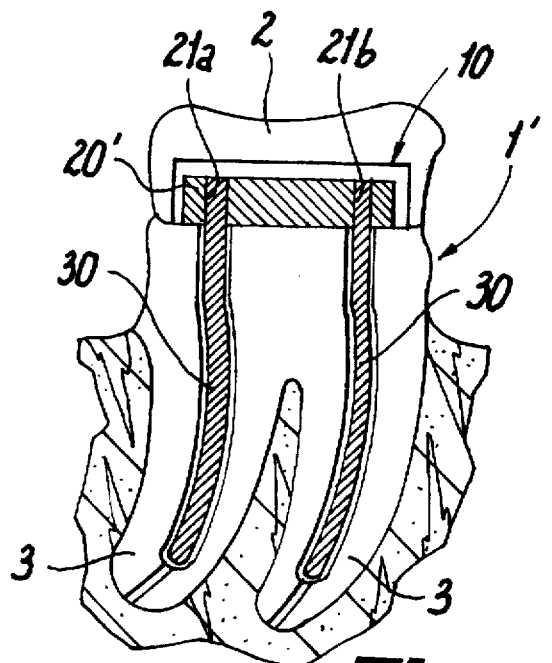
FIG. 2 is a lateral cross-sectional view of a first preferred embodiment of the present invention in a double-canal tooth.

A second dental post and core system 2 for multi-rooted teeth, as illustrated in FIG. 2, may have a second core spacer 20' wherein the respective first and second bores 21a, 21b are sized differently for placement of reinforcing rods 30 of a different size. Prefabricated multiple root dental post and core systems 2 having differently sized reinforcing rods 30 will be multicolored in accordance with the above protocol. For example, a second core spacer 20' may have a yellow ring around first bore 21a and a white ring around second bore 21b to indicate that this core spacer 20' is to be utilized with a 0.040 inch reinforcing rod 30 in first bore 21a and a 0.036 inch reinforcing rod 30 in second bore 21b.

Figure 4:
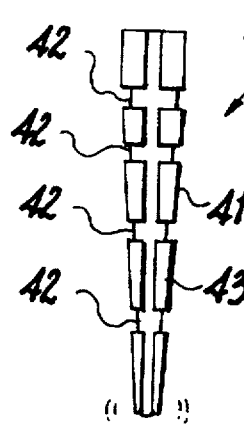
FIG. 4 is a lateral cross-sectional view of a second post reinforcing rod constructed in accordance with the teachings of the present invention.

FIG. 4 illustrates in a front plan view of a second preferred embodiment of a reinforcing rod 40 constructed in accordance with the teachings of the present invention. Second reinforcing rod 40 is a tapered, flexible elongated member 41. The outer wall of the elongated member 41 includes a plurality of displaced circumferential serrations 42 and a channel 43 extending longitudinally between the respective serrations 42. The combination of flexibility in the second reinforcing rod 40 and the displacement of the respective serrations 42 is believed to reduce the wedging effect of rigid posts as known in the art. It is also known that alternatively serrations which are not circumferential may also be employed, such as arcuate segments or threaded indentations.

Figure 5:
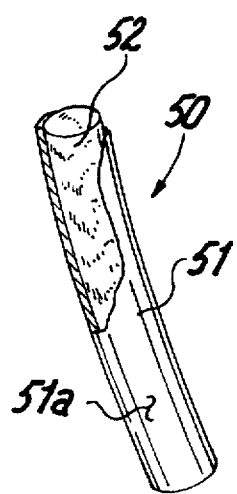
FIG. 5 is a partially cross-sectioned perspective view of a third post reinforcing rod constructed in accordance with the teachings of the present invention.

A third preferred embodiment of a reinforcing rod 50 is illustrated in FIG. 5. Third reinforcing rod 50 comprises a closed flexible sheath 51 having a compressible gel 52 disposed within the interior of the sheath 51. During placement of the third reinforcing rod 50, the wall 51a of the sheath 51 deforms to the varying diameter and curvature of the root canal.

From the foregoing, it should be readily understood that the respective first, second and third reinforcing rods 30, 40 and 50 may be utilized in conjunction with a core spacer 20 or a prefabricated or built-up core 10 may be attached directly to the coronal end of the reinforcing rod 30, 40, 50.

A prefabricated core 10 for attachment directly to a reinforcing rod 20, 40, 50 may include a bore 21 extending therethrough, as illustrated for the core spacer 20 of the present invention. Reinforcing rods 30, 40 find 50 may be pre-cut or formed in an extended length to provide a margin of safety for mistakes in measuring.

Figure 6:
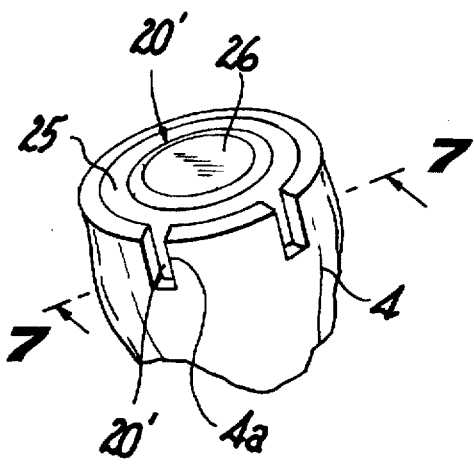
FIG. 6 is a top perspective view of a second built-up core spacer in accordance with the teachings of the present invention.
Figure 7:
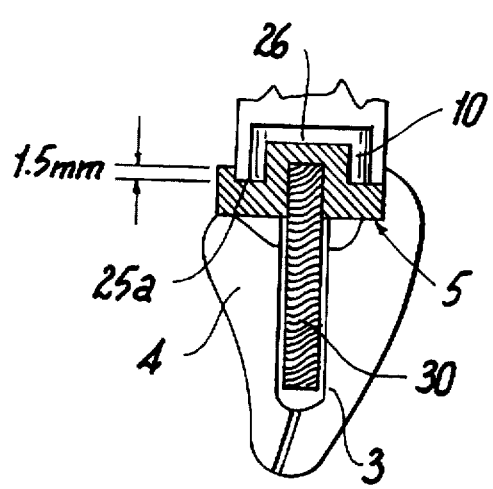
FIG. 7 is a lateral cross-sectional view taken along line 7—7 of FIG. 6.

The core spacer 20 of the present invention may be prefabricated in standard sizes or built-up in the dentist's office. The external shape of core spacer 20 generally corresponds to the concavity of the chamber termed in root canal therapy. In teeth with a shallow concavity, standard dental drills may be used to machine a countersunk region 5 in the tooth (FIG. 7) for receipt of core spacer 20 or a built-up core spacer 20'. FIGS. 6 and 7 illustrate a preferred embodiment of a built-up core spacer 20' constructed in accordance with the teachings of the present invention. The flexible reinforcing rod 30 is placed into the root canal 3 (FIG. 7). Built-up core spacer 20' is then formed about the coronal end of first reinforcing rod 30 by injection of any of the suitable fast-setting liquids or pastes known in the art. Built-up core spacer 20' initially extends to the top of the tooth dentin 4 and into any fractures 4a or the like in the tooth. A recessed ring 25 is then countersunk into the top of the built-up core spacer 20' along the inside edge of the tooth to form a central, raised portion 26 of the built-up core spacer 20'. It is preferred that the floor 25a of the recessed ring 25 is approximately 1.5 mm below the top of the tooth dentin 4. As can be seen in the cross-sectional view of the built-up core spacer 20' illustrated in FIG. 8, a core 10 is seated onto the top of the central, raised portion 26 and the floor 25a of the recessed ring 25. Preferably, sufficient lateral space is left so that the crown 2 may be fitted over the core 10 to likewise rest on the floor 25a of the recessed ring 25, approximately 1.5 mm below the top of the tooth.

Figure 8:
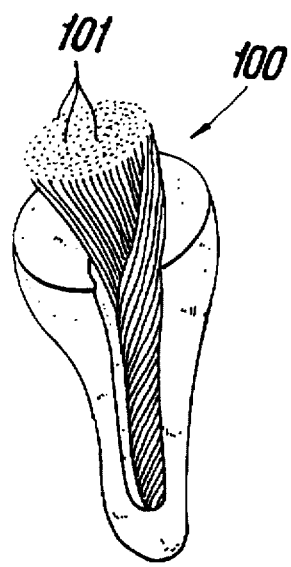
FIG. 8 is a perspective view of a second preferred embodiment of the dental post and core system of the present invention.
Figure 9:
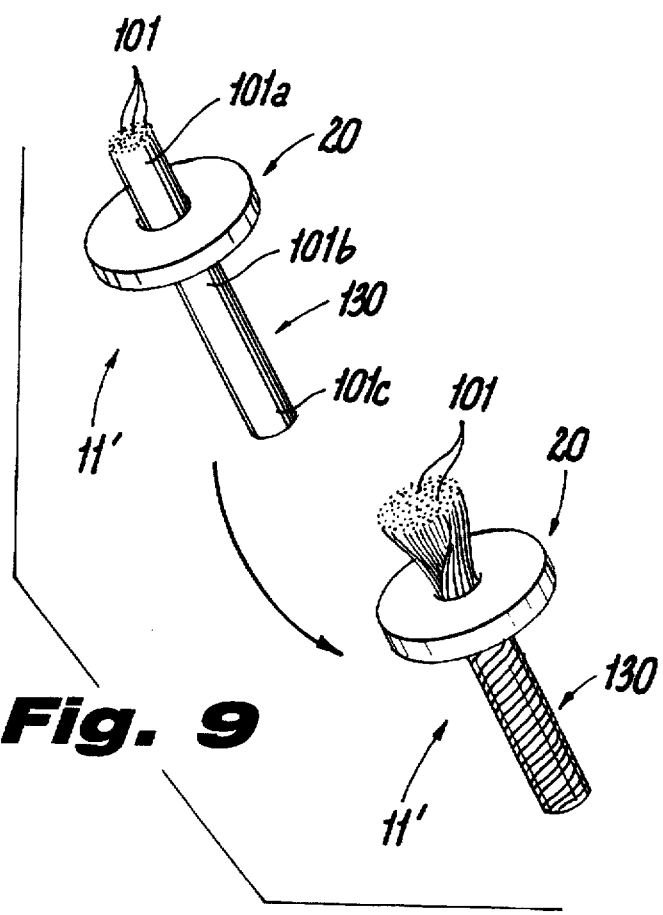
FIG. 9 is a perspective view of a third preferred embodiment of the dental post and core system of the present invention.

A mutable flexible post 100 is illustrated in FIG. 8 and a mutable post reinforcing rod 130 is illustrated in FIG. 9. Mutable post 100 and mutable post reinforcing rod 130 are preferably formed from a bundle of reinforced plastic or other fibers 101 cemented together at the central portion 101b and the lower portion 101c of tile fibers 101. The upper portion 101a of the fibers 101 is loosely compacted so that the upper portion 101a may be selectively flared to provide additional surface area to scaffold a built-up core. Flaring of the upper portion 101a of the fibers 101 may be performed at the factory or in the dentist's office using standard crimping pliers. A prefabricated core (not shown) may be attached to the coronal aspect of the mutable post 100 when it is disposed in its unflared position.

As shown in FIG. 9 the mutable reinforcing rod 130 constructed in accordance with the teachings of the present invention may likewise be utilized in a flared or unflared position. A first core spacer 20 is attached to the coronal end of the mutable reinforcing rod 130. The mutable post 11' comprising a first core spacer 20 and a mutable reinforcing rod 130, may be used to support a prefabricated core, or the coronal end of the mutable post 11' may be flared to form a scaffold for a built-up core. An advantage of this preferred embodiment of the present invention is that a single construction can be used for either a prefabricated dental post and core system or a mutable post reinforcing rod 130 to support a built-up core.

Post 11 may be made without core spacer 20. Moreover, post 11 may be made from a material having a plurality of distributed fibers, wherein at least one of the fibers extends non-axially aligned with respect to a straight axis extending from the apical end to the opposite coronal end of a root of a tooth. For example, the fibers of post 11 may be a bundle of fibers, a longitudinally twisted bundle, a twisted braid, a woven lattice, a helically wrapped bundle of fibers, or a composite of randomly dispersed fibers in a binder.

In each case, at least one of the fibers of post 11 extends non-axially aligned with respect to the straight axis of a root of a tooth.

Figure 10A:
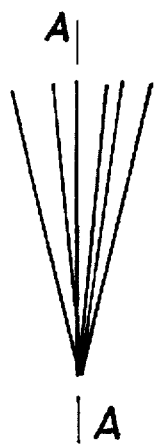
FIGS. 10A–10I show various embodiments for a dental post and core system wherein at least one or more of the fibers constituting the post are non-axially aligned with respect to axis A—A extending from the coronal end to the apical end of a root of a tooth.

For example, in a bundle of fibers, such as the conical bundle of fibers shown in FIG. 10A, while some of the fibers may extend parallel to the straight axis A—A of the root, at least one or more of the fibers extend in a non-axial direction which is not parallel to straight axis A—A of a root of a tooth. That is, at least one or more of the fibers extends in a transverse or angled direction away from the straight axis A—A of the root of a tooth.

Figure 10B:
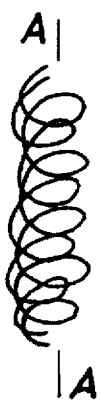
Figure 10C:
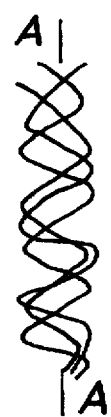
Figure 10D:
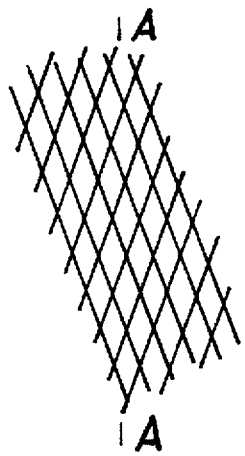
Figure 10E:
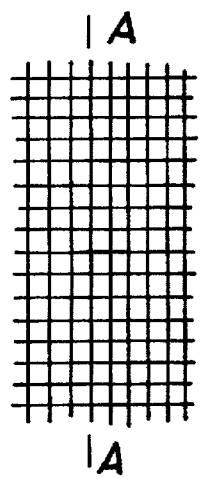
Figure 10F:
Figure 10I:
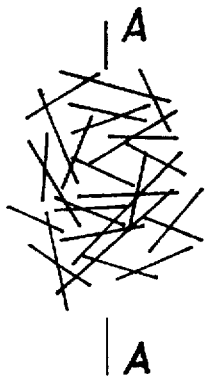
Figure 10H:

With respect to a longitudinally twisted bundle, such as shown in FIG. 10H, a twisted braid, such as shown in FIG. 10C, a helically wrapped bundle of fibers, such as shown in FIG. 10B, the twisting or helical wrap of the fibers causes many, but not necessarily all, of the fibers to extend non-axially.

Figure 10G:

Concerning a woven lattice of fibers, such as shown in FIGS. 10D or 10E, while one set of fibers could extend axially parallel to the straight axis A—A of the root, the other intersecting set of fibers extends in a direction which is non-axially aligned with respect to the straight axis A—A of the root. Moreover, as shown in FIG. 10G, even if most of the weft of a weave of a plurality of fibers extends parallel to the straight axis A—A of the root, at least one or more fibers constituting the warp of the weave of fibers extends non-axially with respect to the straight axis of the root of the tooth. Furthermore, as shown in FIG. 10F, instead of a true weave, a bundle of axially aligned fibers may have at least one or more non-axially aligned fibers constituting a strap collar containing the remaining fibers (whether axially aligned or not) therein.

While the bundles of fibers shown in FIGS. 10A–10I are shown without core spacers, such as core spacer 20 in FIG. 1, similar core spacers may alternately be provided, or the ends of the bundles of fibers may be flared, such as shown in the conical bundle in FIG. 10A or the twisted bundle shown in FIG. 10H.

As shown in FIG. 10I, concerning a composite of randomly dispersed fibers, there is always the possibility of one or more of the fibers being axially aligned to the straight axis A—A of the root of a tooth. However, in order to be randomly dispersed, at least one or more of the fibers extends non-axially with respect to the straight axis A—A of the root of a tooth.

The fibers in FIGS. 10A–10I may be formed from metal or non-metallic fibers in a composite, such as within a plastic material. Alternately, the coronal end may be flared by loose compacting of the coronal end, or by mechanical undercutting of the coronal end.

In addition, the post is both flexible and inelastic, so that the post can bend but generally maintain its original length. For example, in flexing, one side is extended, and the other side is compressing about an axis.

Figure 11:
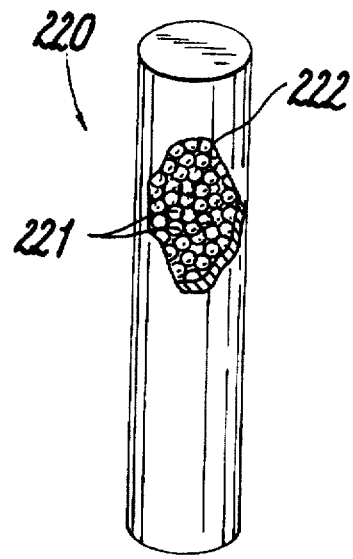
FIG. 11 is a perspective view in partial section of an alternate embodiment for a flexible inelastic post with a plurality of randomly dispersed particles within a binder.

FIG. 11 is a perspective view in partial section of a further alternate embodiment for a flexible inelastic post 220 with a plurality of randomly dispersed particles 221, such as beads or other shaped particles, within a binder 222.

The flexible post of the present invention also leads to improved methods of endodontia that eliminate drilling for post placement.

Various changes, additions and modifications of the present invention may be made to the preferred embodiments without departing from the spirit and scope of the present disclosure. Such changes, additions find modifications within a fair reading of the following claims are intended to be part of the present invention.

Therefore, in view of the foregoing, we claim:

1. A dental post and core device comprising inelastic flexible post means automatically adjusting to the contours of a root canal during placement, said post means comprising a post having a coronal end and an apical end and including a plurality of fibers, wherein at least one of said fibers extends non-axially with respect to a straight axis extending between the coronal and the apical end of said post.

2. The device as in claim 1 wherein a plurality of fibers extends non-axially with respect to the straight axis extending between the coronal end and the apical end of said post.

3. The dental post and core device as in claim 1, wherein said inelastic flexible post includes a binder holding said fibers, wherein further said post is formed from reinforced plastic material.

4. The device of claim 3 wherein the reinforced plastic material is comprised of a material selected from the group consisting of fiberglass polyester composites; ceramic resin dental composites; graphites; graphite composites; teflons; polycarbonates; silicon carbide, polyamides, zirconium composites and aluminum silicate composites.

5. The device of claim 3 wherein said binder is a resin.

6. The device of claim 3 wherein said binder is selected from the group consisting of BIS-GMA resins, urethane and acrylic resins.

7. The device as in claim 1 wherein said inelastic flexible post comprises non-axially aligned fibers in a conical shape.

8. The device as in claim 1 wherein said inelastic flexible post comprises non-axially aligned fibers in a helical wrapped shape.

9. The device as in claim 1 wherein said inelastic flexible post comprises non-axially aligned fibers in a twisted bundle.

10. The device as in claim 1 wherein said inelastic flexible post comprises non-axially aligned fibers in a twisted braid.

11. The device as in claim 1 wherein said inelastic flexible post comprises non-axially aligned fibers which are randomly dispersed fibers in a binding material.

12. The device as in claim 1 wherein said inelastic flexible post comprises a weave including a warp and a weft, wherein at least one of said fibers extends non-axially aligned.

13. The device as in claim 12, wherein a plurality of said fibers extends non-axially aligned.

14. The device as in claim 1 wherein the coronal end is flared.

15. The device of claim 14, wherein said flare of said coronal end is disposed between a neck of said post and the coronal end.

16. The device of claim 1 further having a core spacer about said post, said core spacer being radially disposed about said post substantially at a neck of said post.

17. The device of claim 16 wherein said post and said core spacer are comprised of the same materials.

18. The device of claim 16 wherein said post and said core spacer are integral in a single unit.

19. The device of claim 16 wherein said post and said core spacer are comprised of differing materials.

20. The device of claim 1 where the inelastic flexible post is formed from metal fibers, metal oxides and metal salts secured in a suitable binder.

21. The device of claim 20 wherein the metal fibers are comprised of a material selected from the group consisting of titanium, steel, stainless steel, gold, platinum, silver and palladium.

22. The device of claim 20 wherein the metal fibers are comprised of an alloy of a material selected from the group consisting of titanium, steel, stainless steel, gold, platinum, silver and palladium.

23. The device of claim 1 comprising a suitable amount of radiopaque material so as to render the device opaque to radiographic imaging.

24. The device of claim 23 wherein said radiopaque material is comprised of a material selected from the group consisting of titanium oxide, barium sulfate, precipitated silver and metals.

25. The device of claim 1 wherein said post has a lower portion and an upper portion with an area of flexural stress therebetween, the lower portion being disposed below said area of flexural stress and the upper portion being disposed above said area of flexural stress.

26. The device of claim 25 wherein the lower fibers are cemented and the upper fibers are loosely compacted, the loose compacting comprising the flare at the coronal end thereof.

27. The device of claim 26 wherein the loose compacting may be selectively flared by the user to vary the coronal surface area of the flared loosely compacted fibers, so as to scaffold a built-up tooth core for a tooth being restored.

28. The device of claim 25 wherein the lower fibers are cemented and the upper fibers are mechanically undercut.

29. The dental post and core device as in claim 1, wherein said inelastic flexible post further includes a core spacer, siad flexible post extending apically from said core spacer, said flexible post further inlcuding a core being attachable to an upper portion of said core spacer.

30. An improvement in the post of a dental post and core device as in claim 1, wherein said post includes a plurality of serrations therein.

31. The device as in claim 1, wherein said post bears a color simulating a natural tooth.

32. A flexible post in a dental post and core system wherein said post comprises a laterally-deformable sheath and a compressible gel disposed within said sheath.

33. The flexible post in a dental post and core system as in claim 32, wherein said flexible post further includes a core spacer, said reinforcing rod extending apically from said core spacer, said flexible reinforcing rod further including a core being attachable to an upper portion of said core spacer.

34. A flexible post in a dental post and core system wherein said flexible post is cylindrical along its entire length, automatically adjusts to the contours of a root canal during placement, and comprises a bundle of flexible fibers.

35. A dental post and core system having an ineslastic flexible post wherein said inelastic flexible post is formed from reinforced plastic material and wherein a coronal end of said inelastic flexible post is flared outward.

36. A dental post and core system as in claim 35 wherein said reinforced plastic material comprises a fiberglass polyester composite.

37. An improvement in the post of a dental post and core system comprising a flexible inelastic post cylindrical along its entire length, said post comprising a bundle of flexible fibers, and spacer means mounted on said post for absorbing intracanal stresses comprising a core spacer for absorbing said stresses by deformation thereof.

38. An improvement in the post of a dental post and core system as in claim 37, siad improvement further comprising said post extending apically from the core spacer, said post having a core being attachable to an upper portion of said core spacer.

* * * * *